(12) United States Patent
Hassler et al.

(10) Patent No.: US 8,088,168 B2
(45) Date of Patent: Jan. 3, 2012

(54) IMPLANT, MORE PARTICULARLY PARTIAL ULNAR HEAD IMPLANT

(75) Inventors: Michel Hassler, Saint-Ismier (FR); Cécile Real, Grenoble (FR); Marc Garcia-Elias, Matadepera (ES)

(73) Assignee: Tornier SAS, Saint Ismier (FR)

( * ) Notice: Subject to any disclaimer, the term of this patent is extended or adjusted under 35 U.S.C. 154(b) by 459 days.

(21) Appl. No.: 12/121,084

(22) Filed: May 15, 2008

(65) Prior Publication Data

US 2008/0249631 A1 Oct. 9, 2008

Related U.S. Application Data

(63) Continuation-in-part of application No. PCT/IB2006/003190, filed on Nov. 14, 2006.

(30) Foreign Application Priority Data

Nov. 17, 2005 (FR) ...................................... 05 11671

(51) Int. Cl.
*A61F 2/42* (2006.01)
(52) U.S. Cl. ................................................... 623/21.12
(58) Field of Classification Search .... 623/20.11–20.17, 623/20.33
See application file for complete search history.

(56) References Cited

U.S. PATENT DOCUMENTS

| | | | |
|---|---|---|---|
| 3,526,005 A | 9/1970 | Bokros et al. | |
| 3,707,006 A | 12/1972 | Bokros et al. | |
| 3,745,590 A | 7/1973 | Stubstad | |
| 3,924,276 A | 12/1975 | Eaton | |
| 4,005,163 A | 1/1977 | Bokros | |
| 4,164,793 A | 8/1979 | Swanson | |
| 4,166,292 A | 9/1979 | Bokros | |
| 4,198,712 A | 4/1980 | Swanson | |
| 4,259,752 A | 4/1981 | Taleisnik | |
| 4,645,505 A * | 2/1987 | Swanson | 623/21.12 |
| 4,784,661 A | 11/1988 | Beckenbaugh et al. | |
| 4,936,860 A | 6/1990 | Swanson | |
| 4,955,915 A | 9/1990 | Swanson | |
| 5,108,444 A * | 4/1992 | Branemark | 623/21.12 |
| 5,314,485 A * | 5/1994 | Judet | 623/21.13 |

(Continued)

FOREIGN PATENT DOCUMENTS

DE 29721522 2/1998

(Continued)

OTHER PUBLICATIONS

Allieu et al., "Swanson Trapezial Implant in the Treatment of Peritrapezial Arthrosis—A study of eight cases," Ann. Chir. Main, vol. 3, No. 2, 1984, pp. 113-123.

(Continued)

*Primary Examiner* — Alvin J. Stewart
(74) *Attorney, Agent, or Firm* — Faegre & Benson LLP

(57) ABSTRACT

A method and apparatus for replacing an articular surface of a bone. The implant includes at least one head with a bore and a lateral articular surface generally perpendicular to an axis of the bore. A holding element includes a stem at a proximal end adapted to attach to the bone. A member at a distal end of the holding device is adapted to engage with the bore in the head so that the lateral articular surface is positioned to engage transverse loads. The bore permits limited lateral translation of the head in at least one direction generally perpendicular to a longitudinal axis of the member.

24 Claims, 4 Drawing Sheets

U.S. PATENT DOCUMENTS

| | | | |
|---|---|---|---|
| 5,326,364 | A | 7/1994 | Clift, Jr. et al. |
| 5,645,605 | A | 7/1997 | Klawitter |
| 5,702,469 | A | 12/1997 | Whipple et al. |
| 5,702,472 | A | 12/1997 | Huebner |
| 5,728,163 | A | 3/1998 | Maksene |
| 5,743,918 | A | 4/1998 | Calandruccio et al. |
| 5,780,119 | A | 7/1998 | Dearnaley et al. |
| 5,782,926 | A | 7/1998 | Lamprecht |
| 5,782,927 | A | 7/1998 | Klawitter et al. |
| 5,951,604 | A * | 9/1999 | Scheker ............... 623/21.11 |
| 6,159,247 | A | 12/2000 | Klawitter et al. |
| 6,168,630 | B1 * | 1/2001 | Keller et al. ............. 623/21.11 |
| 6,217,616 | B1 | 4/2001 | Ogilvie |
| 6,296,666 | B1 * | 10/2001 | Gardner ............... 623/20.29 |
| 6,383,223 | B1 * | 5/2002 | Baehler et al. ........... 623/21.11 |
| 6,454,808 | B1 * | 9/2002 | Masada ............... 623/21.15 |
| 6,699,292 | B2 | 3/2004 | Ogilvie et al. |
| 6,814,757 | B2 | 11/2004 | Kopylov et al. |
| 6,890,358 | B2 * | 5/2005 | Ball et al. ............. 623/21.13 |
| 7,025,789 | B2 * | 4/2006 | Chow et al. ............ 623/21.11 |
| 7,025,790 | B2 * | 4/2006 | Parks et al. ............ 623/21.18 |
| 7,625,408 | B2 * | 12/2009 | Gupta et al. ........... 623/21.11 |
| 7,708,781 | B2 * | 5/2010 | Scheker ............... 623/20.11 |
| 7,722,676 | B2 * | 5/2010 | Hanson et al. .......... 623/21.12 |
| 2001/0025199 | A1 * | 9/2001 | Rauscher .............. 623/21.13 |
| 2002/0082705 | A1 * | 6/2002 | Bouman et al. ......... 623/21.11 |
| 2004/0138756 | A1 * | 7/2004 | Reeder ................ 623/21.11 |
| 2005/0033426 | A1 | 2/2005 | Ogilvie et al. |
| 2005/0171613 | A1 * | 8/2005 | Sartorius et al. ........ 623/21.13 |
| 2006/0030946 | A1 * | 2/2006 | Ball et al. ............. 623/21.13 |
| 2007/0198095 | A1 | 8/2007 | VanDer Meulen et al. |
| 2007/0225820 | A1 | 9/2007 | Gareth et al. |
| 2009/0204224 | A1 * | 8/2009 | Berelsman et al. ....... 623/21.14 |
| 2009/0254189 | A1 * | 10/2009 | Scheker ............... 623/21.11 |

FOREIGN PATENT DOCUMENTS

| | | |
|---|---|---|
| DE | 19925529 | 12/2000 |
| FR | 2680967 | 3/1993 |

OTHER PUBLICATIONS

Shui et al., "High-Strength, high-surface-area, porous carbon made from submicron-diameter carbon filaments," Carbon, vol. 34, issue 9, 1996, pp. 811-814.

Pequignot et al., "Partial Prosthesis of Scaphoid from Silastic to Pyrocarbon," Journal of Hand Surgery, vol. 228 supplement, Fourth Congress of F.E.S.S.H., Bologna, Italy, Jun. 1997, 2 pp.

Commercial brochure entitled "Scaphoid Partial Implant: An Alternative to Arthrodesis," presented at a Paris trade fair on Dec. 12, 1996, 2 pp.

International Search Report from international application No. PCT/IB02/05189, mailed Feb. 2, 2003, 2 pp.

Calandruccio et al, "Anthroplasty of the Thumb Carpometacarpal Joint," Seminars in Arthroplasty, vol. 8, No. 2, Apr. 1997, pp. 135-147.

French Preliminary Report on Patentability with Written Opinion (and English translation of written opinion) from international application No. PCT/IB2006/003190, dated Jul. 8, 2008, 5 pp.

Gordon et al., "Kinematics of Ulnar Head Arthroplasty," Journal of Hand Surgery, vol. 28b, No. 6, Dec. 6, 2003, pp. 551-558.

\* cited by examiner

85%  15%

IMPLANT, MORE PARTICULARLY PARTIAL ULNAR HEAD IMPLANT

The present application is a continuation-in-part of International Application PCT/IB2006/003190, entitled Implant, More Particularly Partial Ulnar Head Implant, with an international filing date of Nov. 14, 2006, which claims the benefit of French application no. 0511671, entitled Implant, Notamment Implant Partiel De La Tete du Cubitus, filed Nov. 17, 2005, the complete disclosures of which are hereby incorporated by reference.

FIELD OF THE INVENTION

The present invention relates of an implant, and more particularly a partial ulnar head implant.

BACKGROUND OF THE INVENTION

A partial implant for the ulnar head has been described in an article of K. D. Gordon et al. with the title "Kinematics of ulnar head arthroplasty" that was published in *The Journal of Hand Surgery*, Vol. 28B, No. 6, December 2003. It comprises a hemispherical head intended as a replacement for the articular segment of the ulnar head, that is, the lateral segment of the distal end of the ulna articulated with the radial head. The hemispherical head is fitted onto the end of a stem, and rigidly fastened there with a screw, the stem in turn being intended to be rigidly fastened inside of a hole formed in the ulna so as to hold the implant in place.

Contrary to a total ulnar head implant, such a partial implant allows the triangular ligament linking the ulnar head and radius as well as the ulnocarpal ligament linking the ulna and the wrist, to be preserved and the interostal membrane linking ulna and radius, to be kept under tension. Hence, the stability of such a partial implant is distinctly superior to that of a total implant.

The ulnar head is known to be subject, more to transverse than to axial loads. It has actually been observed that only about 15% of the axial loads that are applied to the distal end of the fore-arm are taken up by the ulna, the other about 85% are taken up by the radius. The transverse loads are particularly high during fore-arm rotations (pronation, supination). For illustration, FIGS. 6 and 7 are representations of the axial loads taken up by ulna and radius in a vertical position of the hand (FIG. 6), and of the transverse loads mutually applied by the ulnar head and radial head in a horizontal position of the fore-arm (FIG. 7).

In the case of the partial implant mentioned above, the transverse loads taken up by the head of the implant are transmitted to the stem. It follows that the remaining segment of the ulnar head as well as the surrounding ligaments are no longer subject to the loads taken up by them initially. Not any longer under pressure, the remaining segment of the ulnar head is condemned to undergo progressive decalcification, and the surrounding ligaments, to lose their vigor.

BRIEF SUMMARY OF THE INVENTION

The present invention is directed to a method and apparatus to replace an articular surface of a bone.

In one embodiment, the implant includes at least one head with a bore and a lateral articular surface generally perpendicular to an axis of the bore. A holding element including a stem at a proximal end adapted to attach to the bone is provided. A member at a distal end of the holding device is adapted to engage with the bore in the head so that lateral articular surface is positioned to engage transverse loads. The bore permits limited lateral translation of the head in at least one direction generally perpendicular to a longitudinal axis of the member.

The bore preferably permits lateral translation of the head in any direction generally perpendicular to the longitudinal axis of the member. The head optionally includes a generally lateral planar face generally perpendicular to the axis of the bore and opposite the lateral articular surface. In one embodiment, the bore includes a generally circular cross section and the member includes a cylindrical pin, wherein the circular cross section of the bore has a diameter greater than a diameter of the cylindrical pin.

The lateral articular surface is preferably pyrocarbon. In one embodiment, the entire head comprises pyrocarbon. In one embodiment, the stem of the holding member is elastically deformable.

The implant can serve as a complete or partial ulnar head implant. The head is preferably retained to the member solely by a triangular ligament. The stem and the longitudinal axis of the member are preferably adapted to be oriented generally parallel to the bone.

A plurality of heads is preferably provided. In one embodiment, a distance from the axis of the bore to the lateral articular surface varies in at least two heads. In another embodiment, the lateral articular surface varies in at least two heads.

The present invention is also directed to a method of replacing an articular surface on a head of a bone. The method includes resecting an articular surface of a bone while preserving a portion of the head. A stem of a holding element is implanted in the bone so that a member at a distal end of the holding element is located proximate the resected articular surface. A bore in a head is engaged with the member so that a lateral articular surface on the head is generally perpendicular to an axis of the bore and positioned generally at the location of the resected articular surface to engage with transverse loads. The head is permitted to translate laterally in at least one direction generally perpendicular to a longitudinal axis of the member.

In one embodiment, a surface on the head generally opposite the lateral articular surface is engaged with a preserved portion of the head. In embodiments including a partial ulnar head implant, the head is preferably retained to the member solely by a triangular ligament.

Although the present method and implant is primarily discussed as a partial ulnar head implant, the present method and apparatus applies equally well to heads in other locations of a patient's body without departing from the intended scope of the present invention. For example, the method and implant may be modified to repair articular surfaces on the proximal or distal femur, proximal or distal radius, etc.

To this end an implant is proposed, and more particularly a partial ulnar head implant, that comprises a head intended to replace at least a lateral articular segment of a bone taking up transverse loads, and a holding element connected to the head and intended to be fastened to that bone, characterized in that the head is mobile in translation relative to the holding element in at least one direction that corresponds to a direction of the transverse loads when the implant is in place in the patient.

Thanks to this lateral mobility of the implant's head, the latter can rest against the remaining segment of the bone onto which it is mounted, and/or against the surrounding ligaments, when the patient moves, and can thus transmit to them the transverse loads received. Preferably, the head of the implant is made of pyrocarbon, and its outside surface is polished, in order to avoid its wear during its displacements relative to the holding element, as well as the wear of the neighboring bones.

The holding element advantageously is a stem having its axis transverse to the direction mentioned before, and is conceived to be held, simply by elastic deformation in a hole made in advance in the bone. This stem is rigidly connected with a pin, for instance, that is engaged in a bore of the head while the transverse mobility of the head relative to the stem is gained by play existing between the pin and the head. Preferably, the corresponding cross sections of the pin and bore are both circular while that of the pin has a smaller diameter than that of the bore.

BRIEF DESCRIPTION OF THE SEVERAL VIEWS OF THE DRAWING

Further characteristics and advantages of the present invention will become apparent when reading the following detailed description that is given while referring to the schematic drawings.

DETAILED DESCRIPTION OF THE INVENTION

Figure 1:
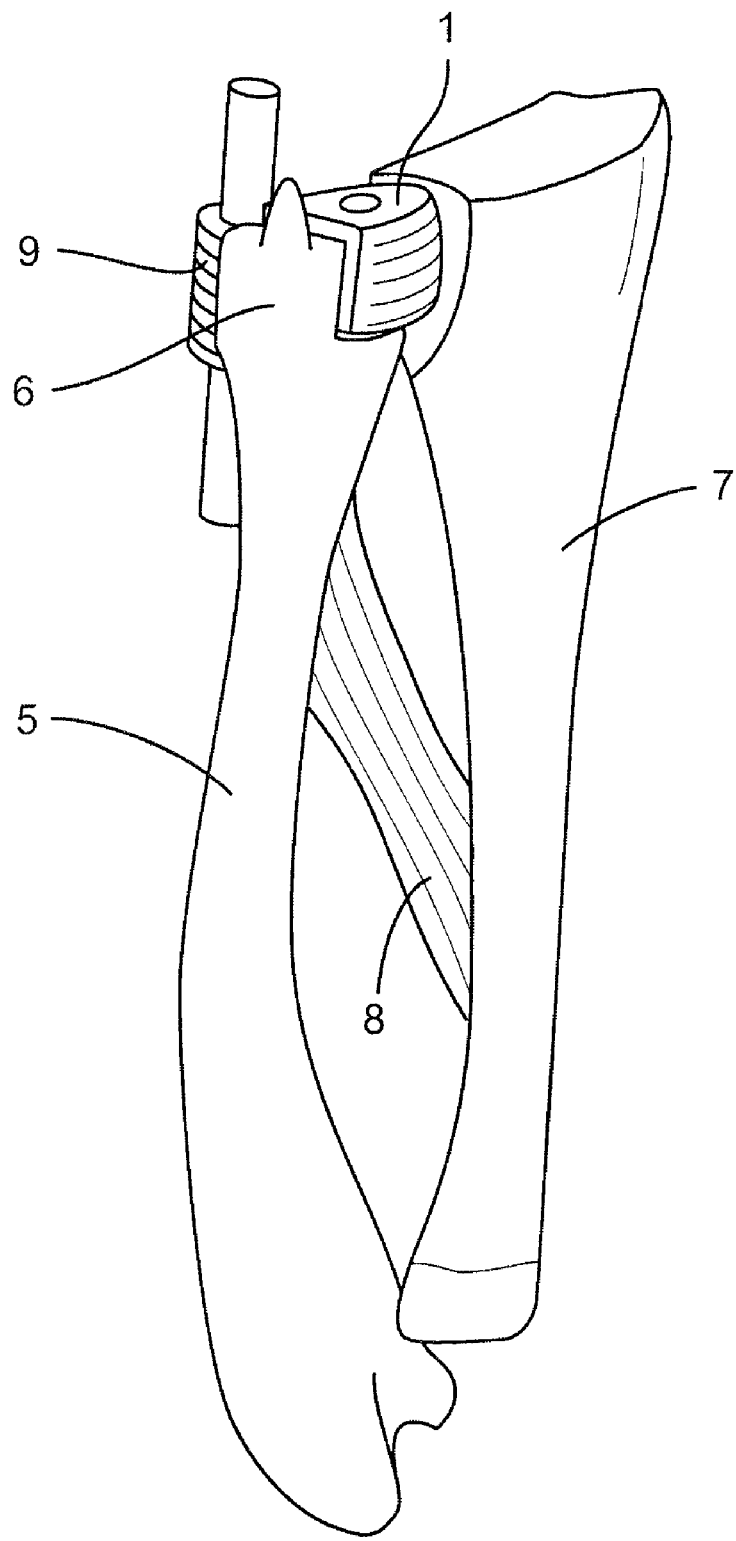
FIG. 1 is a perspective view of radius, ulna, and a partial implant replacing the articular segment of the ulnar head according to an embodiment of the present invention.
Figure 2:
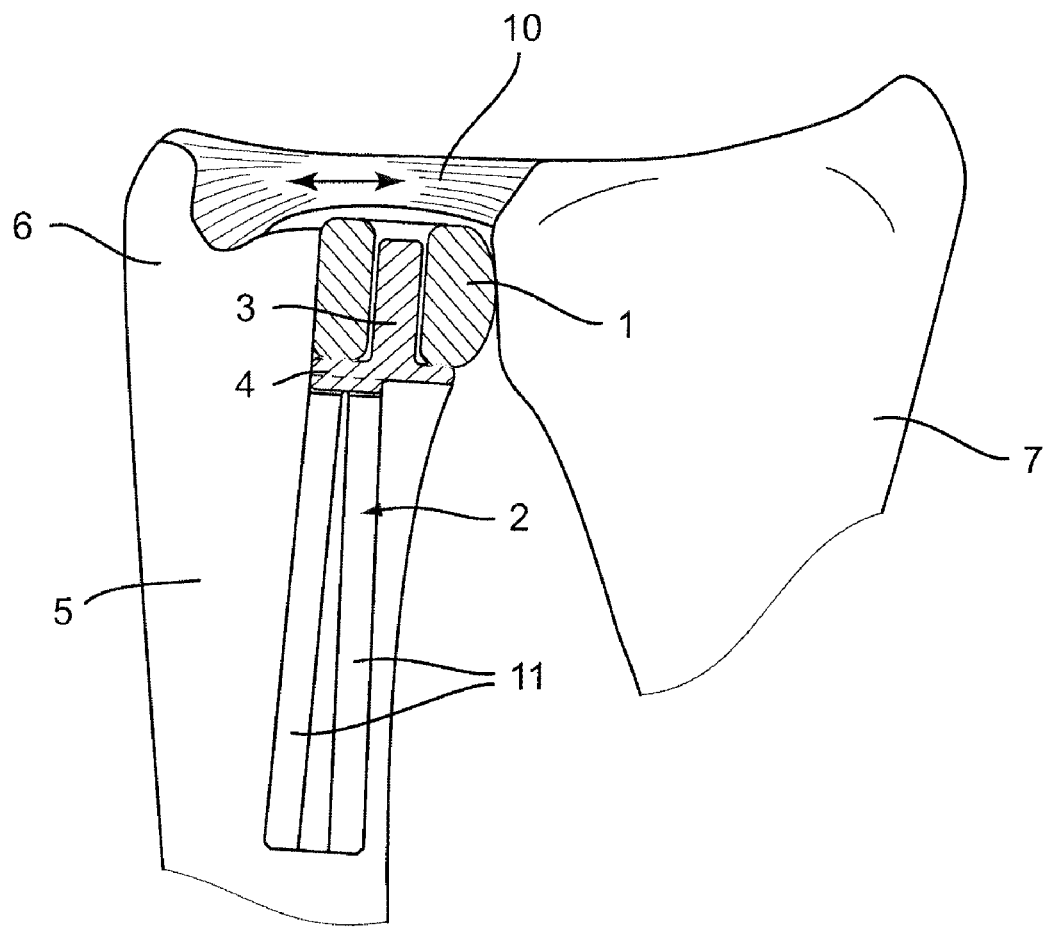
FIG. 2 is a front view of the distal end of radius and ulna and of a partial implant replacing the articular segment of the ulnar head according to an embodiment of the present invention.
Figure 3:
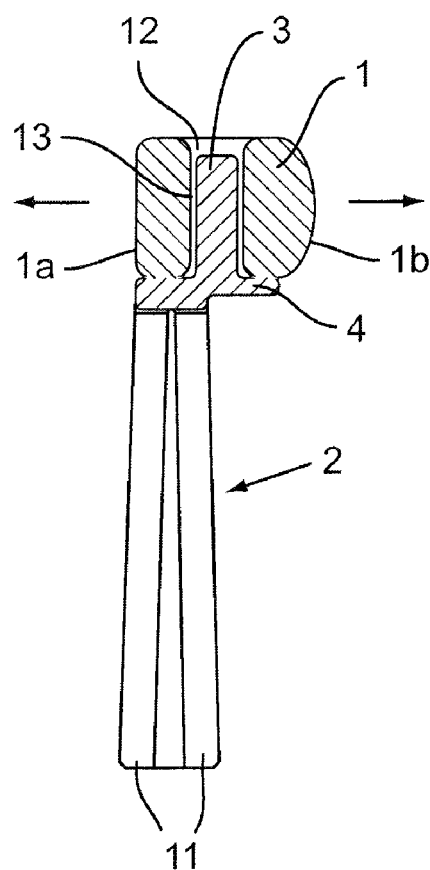
FIG. 3 is a sectional view of the partial implant taken along axis III-III of FIG. 5.
Figure 4:
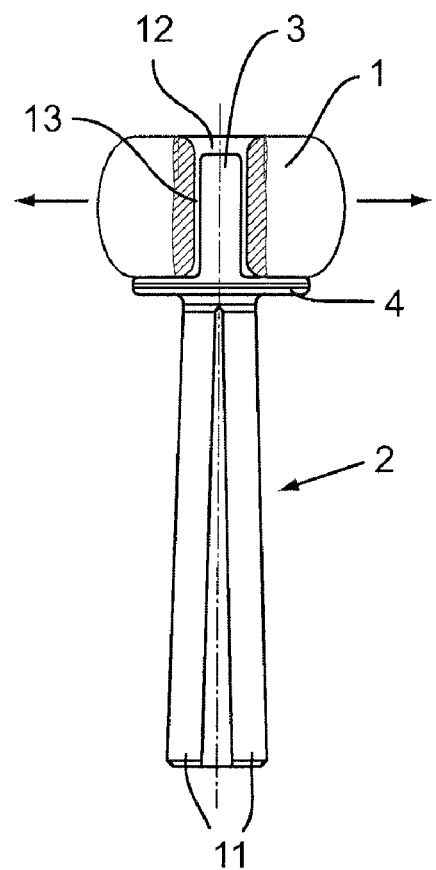
FIG. 4 is a plane view, partly sectioned, of the partial implant in the direction of arrow IV in FIG. 5.
Figure 5:
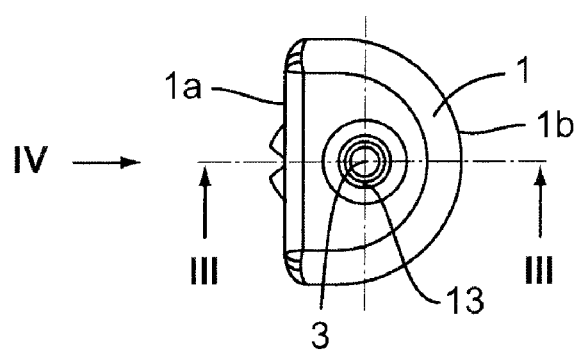
FIG. 5 shows the partial implant seen from above according to an embodiment of the present invention.
Figure 6:
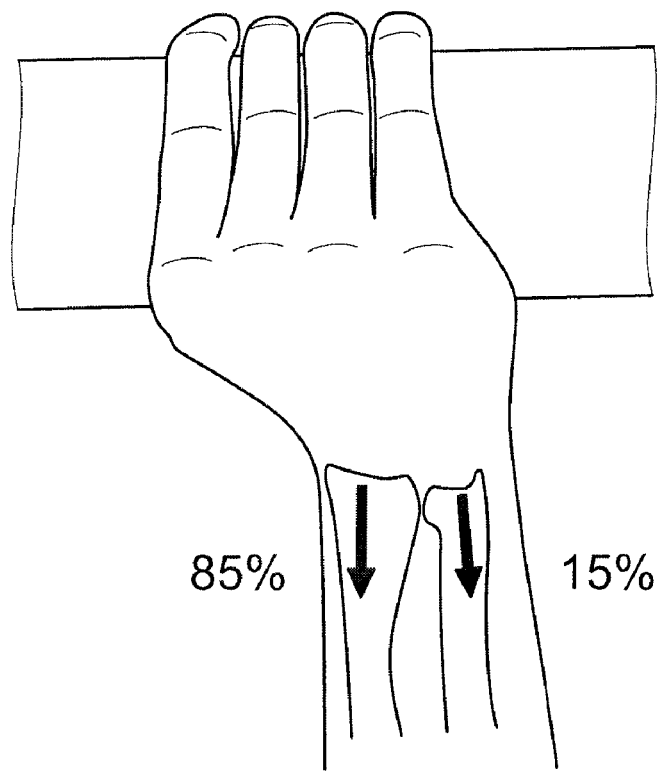
FIG. 6 illustrates distribution of the axial loads taken up by the distal end of radius and ulna in a vertical position of the hand.
Figure 7:
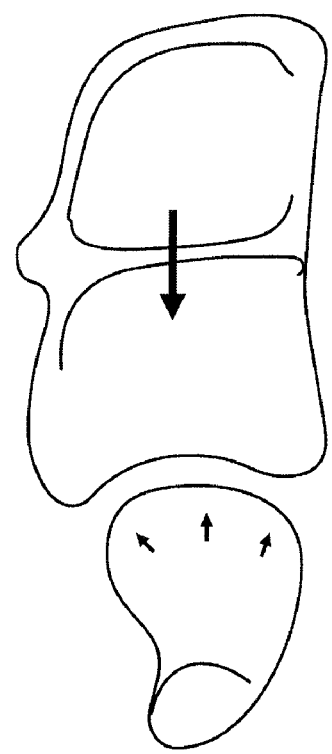
FIG. 7 illustrates the transverse loads applied between the radial head and the ulnar head in a neutral position of pronosupination with the fore-arm horizontal.

Referring to FIGS. 1 to 5, a partial ulnar head implant according to the invention comprises a head 1 connected to a stem 2 by means of a pin 3 projecting from a plate 4 situated at one end of stem 2. The axis of pin 3 is parallel to that of stem 2, but does not coincide with it. Head 1 is intended to be placed into a space that is obtained by taking off the articular segment of the ulnar head, as shown in FIGS. 1 and 2 where the reference numeral 5 designates the ulna, the reference numeral 6 designates the remaining segment of the ulnar head, the reference numeral 7 designates the radius, the reference numeral 8 designates the interostal membrane, the reference numeral 9 designates the sheath of the posterior ulnar tendon, and the reference numeral 10 designates the triangular ligament. As to stem 2, it is intended to be introduced into a corresponding hole formed in advance in the ulna, in order to hold the implant in place.

Stem 2, pin 3 and plate 4 are preferably manufactured from a single piece of material (referred to as monolithic), such as for example, ceramic, polymeric materials, metal, or combinations thereof, and in particular, titanium. Other than conventional implants, the implant according to the invention need not be fastened solidly to the bone onto which it is mounted, here the ulna. Stem 2 is not destined to resist elevated constraints but simply to position the implant, so as to hinder its dislocation during pronating and supinating movements. Thus, this stem 2 may consist of elastic arms 11, four in the example illustrated, that become deformed when inserted into the ulna in order to hold the implant in place, solely by their elastic deformation. One will note that the stability of the implant according to the invention is first of all secured by the remaining segment 6 of the ulnar head and by the surrounding ligaments. The triangular ligament 10 in particular holds the implant in the axial direction (see FIG. 2).

Head 1 of the implant according to the invention is preferably made of pyrocarbon, and its outside surface is polished. Pyrocarbon is known to have a modulus of elasticity (Young's modulus) close to that of bone, so that it may rub against the bone—especially when its surface is polished—without causing wear of the bone or of itself. According to a typical embodiment, head 1 consists of a graphite core covered with a layer of pyrocarbon, the graphite-pyrocarbon combination having a modulus of elasticity (Young's modulus) close to that of bone. According to another embodiment, head 1 is made of solid pyrocarbon, that is, does not have a graphite core.

Essentially, head 1 has the shape of a hemisphere truncated by two mutually parallel planes perpendicular to the plane face of the hemisphere and to the axis of stem 2. The plane face 1a is intended to be positioned facing the remaining segment 6 of the ulnar head. The hemispherical face 1b of the periphery of head 1 is intended to be positioned facing the radial head 7. It will be noted that head 1 need not have a shape precisely respecting the anatomy of the ulnar head, inasmuch as this head 1 is supposed to serve as a part intermediate between the radial head and the remaining segment 6 of the ulnar head, as will be seen below.

A bore 12 is made in head 1 so that it may receive pin 3 so as to link head 1 to stem 2. Conforming to the invention, this bore 12 has a larger cross section than the pin 3, so that gap 13 is created between head 1 and pin 3 making head 1 mobile transversely relative to the axis of stem 2, as shown by arrows in FIGS. 3 and 4. Within the context of the present invention, the notion of transverse mobility is to be understood as a mobility in a plane cutting the axis of stem 2, and running parallel to the transverse loads applied by the radial head while the implant is in place in the patient. In the example illustrated, where stem 2 and pin 3 are parallel, the plane cited is essentially perpendicular to the corresponding axes of stem 2 and ulna.

In a typical embodiment of the present invention, the gap 13 between head 1 and pin 3 is about 1 millimeter. Preferably, the cross-sections of the bore 12 and pin 3 are both circular, but have different diameters, so that head 1 may move in all directions in a plane transverse to stem 2. However, in a variant the cross section of bore 12 could have a different shape, such as oblong, in order to permit preferential movement in a particular direction of transverse movement of head 1.

Pin 3 has the function simply of limiting the transverse movements of head 1. It will be noted that head 1 need not be made axially secured to stem 2. In the preferred embodiment, once the implant is in place the head 1 is axially retained solely by the triangular ligament 10. In cases where the triangular ligament 10 is damaged, one still could provide a variant where head 1 would be axially blocked relative to stem 2, for instance by a bulge around the periphery of pin 3 or by a plate fastened to the end of pin 3 opposite to plate 4.

As indicated before, head 1 of the implant according to the invention is intended to be inserted between the articular segment of radial head 7 and the remaining segment 6 of ulnar head 5, the hemispherical surface 1b of head 1 serving as the surface of articulation with radial head 7. Since the segment 6 of the ulnar head 5 is preserved, the triangular ligament 10 that links ulna and radius, as well as the ulnocarpal ligament (not visible in the drawings) and the sheath of the posterior ulnar tendon 9 are preserved as well and the interostal membrane 8 remains tensioned. All these ligaments 8 to 10 thus may continue fulfilling their intended anatomical functions.

One finds in general that in the case where the ulnar head is affected, the triangular ligament 10 is distended. For head 1 of the implant, therefore, a size in the transverse plane will be selected that is slightly larger than that of the ulnar head segment replaced by it. Thus, by its presence the head 1 keeps the ulnar and radial heads slightly spread apart from each other, relative to their anatomic positions, as shown by double arrows in FIG. 2, so that the triangular ligament 10 is re-tensioned.

The transverse mobility of head 1 relative to the holding stem 2 offers several advantages. In the first place, it reduces the loads taken up by stem 2 while the ulnar head is subject to transverse constraints, and more particularly during rotating movements of the fore-arm (pronation, supination), and raises those taken up by the remaining segment 6 of the ulnar head and the surrounding ligaments. Actually head 1, rather than transmitting to stem 2 the chief part of the transverse constraints received, will come to rest against the remaining segment 6 of the ulnar head and/or against the surrounding ligaments when moving transversely, so that they take up constraints similar to those that they received prior to resection of the articular segment of the ulnar head. The original stability of the ulnar head will thus be respected. The remaining segment 6 of the ulnar head preserves its substance, since it continues to be subject to constraints. The surrounding ligaments that are tensioned by the transverse movements of head 1 will also remain active.

It is a further advantage of the transverse mobility of head 1, or more precisely of the play between head 1 and pin 3, that the surgeon, having introduced stem 2 into the ulna, may easily place a head 1 onto stem 2, and then pull it just as easily away if he has to. The surgeon may thus try several head sizes until he finds that which fits the patient best. Head size may vary in a variety of ways, including the outside diameter of the head 1, off-set distance between the bore 12 and the articular surface 1*b*, shape of the articular surface 1*b*, and the like.

While the present invention has been described above within the context of a partial ulnar head implant, it will be clear that it may be applied in like fashion to any partial or total implant the head of which is intended to replace at least a lateral articular segment of a bone and to take up transverse loads.

Where a range of values is provided, it is understood that each intervening value, to the tenth of the unit of the lower limit unless the context clearly dictates otherwise, between the upper and lower limit of that range and any other stated or intervening value in that stated range is encompassed within the inventions. The upper and lower limits of these smaller ranges which may independently be included in the smaller ranges is also encompassed within the inventions, subject to any specifically excluded limit in the stated range. Where the stated range includes one or both of the limits, ranges excluding either both of those included limits are also included in the inventions.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present inventions are not entitled to antedate such publication by virtue of prior invention. Further, the dates of publication provided may be different from the actual publication dates which may need to be independently confirmed.

Other embodiments of the invention are possible. Although the description above contains many specificities, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims.

What is claimed is:

1. An implant comprising:
   a head adapted to replace at least a lateral articular segment of a bone taking up transverse loads, the head having a lateral articular surface, the lateral articular surface formed by an outer surface of the head that is adapted to withstand the transverse loads, the head further having an engagement surface generally opposite the lateral articular surface that is adapted to engage with a non-resected portion of the bone; and
   a holding element connected with the head that is adapted to be fastened to the bone, wherein the head is mobile in translation relative to the holding element in at least one direction that corresponds to a direction of the transverse loads when the implant is in place in the patient.

2. The implant of claim 1 wherein the lateral articular surface comprises pyrocarbon.

3. The implant of claim 1 wherein the head comprises pyrocarbon.

4. The implant of claim 1 wherein the implant comprises an ulnar head implant.

5. The implant of claim 1 wherein the implant comprises a partial ulnar head implant and the articular surface engages with a radial head.

6. The implant of claim 1 wherein the implant comprises a partial ulnar head implant and the head is retained to the member solely by a triangular ligament.

7. The implant of claim 1 comprising a plurality of heads in which a distance from the axis of the bore to the lateral articular surface varies in at least two heads.

8. The implant of claim 1 comprising a plurality of heads in which a shape of the lateral articular surface varies in at least two heads.

9. An implant to replace a resected articular surface of a partially resected head of a bone, the implant comprising:
 a holding element comprising a stem at a proximal end adapted to attach to the bone and a member at a distal end; and
 a head comprising a bore adapted to engage with the member, a lateral articular surface generally perpendicular to an axis of the bore formed by an outer portion of the head, and positioned generally at the location of the resected articular surface, and a surface on the head generally opposite the lateral articular surface and adapted to engage with a non-resected portion of the head, wherein the bore permits limited lateral translation of the head in at least one direction generally perpendicular to a longitudinal axis of the member in response to transverse loads.

10. The implant of claim 9 wherein the head comprises a generally lateral planar face generally perpendicular to the axis of the bore and opposite the lateral articular surface.

11. The implant of claim 9 wherein the bore comprises a generally circular cross section and the member comprises a cylindrical pin, wherein the circular cross section of the bore has a diameter greater than a diameter of the cylindrical pin.

12. The implant of claim 9 wherein the bore comprises a cross-sectional area greater than a cross-sectional area of the member.

13. The implant of claim 9 wherein the bore permits lateral translation of the head in any direction generally perpendicular to the longitudinal axis of the member.

14. The implant of claim 9 wherein the lateral articular surface comprises pyrocarbon.

15. The implant of claim 9 wherein the head comprises pyrocarbon.

16. The implant of claim 9 wherein the stem comprises an elastically deformable material.

17. The implant of claim 9 wherein the implant comprises an ulnar head implant.

18. The implant of claim 9 wherein the implant comprises a partial ulnar head implant and the articular surface engages with a radial head.

19. The implant of claim 9 wherein the implant comprises a partial ulnar head implant and the head is retained to the member solely by a triangular ligament.

20. The implant of claim 9 wherein the stem and the longitudinal axis of the member are adapted to be oriented generally parallel to the bone.

21. The implant of claim 9 comprising a plurality of heads in which a distance from the axis of the bore to the lateral articular surface varies in at least two heads.

22. The implant of claim 9 comprising a plurality of heads in which a shape of the lateral articular surface varies in at least two heads.

23. An implant to replace an articular surface of a bone, the implant comprising:
 a plurality of heads in which a distance from the axis of the bore to the lateral articular surface varies in at least two heads, the plurality of heads including at least one head comprising an inner bore and an outwardly facing lateral articular surface generally perpendicular to an axis of the bore; and
 a holding element comprising a stem at a proximal end adapted to attach to the bone and a member at a distal end adapted to engage with the bore in the head, the member positioning the lateral articular surface to withstand transverse loads, the bore permitting limited lateral translation of the head in at least one direction generally perpendicular to a longitudinal axis of the member.

24. An implant to replace an articular surface of a bone, the implant comprising:
 a plurality of heads in which a shape of the lateral articular surface varies in at least two heads, the plurality of heads including at least one head comprising an inner bore and an outwardly facing lateral articular surface generally perpendicular to an axis of the bore; and
 a holding element comprising a stem at a proximal end adapted to attach to the bone and a member at a distal end adapted to engage with the bore in the head, the member positioning the lateral articular surface to withstand transverse loads, the bore permitting limited lateral translation of the head in at least one direction generally perpendicular to a longitudinal axis of the member.

* * * * *